(12) United States Patent
Consolaro et al.

(10) Patent No.: US 10,639,839 B2
(45) Date of Patent: May 5, 2020

(54) ASEPTIC CONTAINMENT DEVICE AND PROCESS FOR ITS PRODUCTION AND ASSEMBLY

(71) Applicant: BREVETTI ANGELA S.R.L., Arzignano (IT)

(72) Inventors: Roberto Consolaro, Arzignano (IT); Angelo Consolaro, Arzignano (IT); Rajeev Kabbur, Arzignano (IT)

(73) Assignee: BREVETTI ANGELA S.R.L., Arzignano (VI) (IT)

( * ) Notice: Subject to any disclaimer, the term of this patent is extended or adjusted under 35 U.S.C. 154(b) by 367 days.

(21) Appl. No.: 15/543,951

(22) PCT Filed: Jan. 18, 2016

(86) PCT No.: PCT/IT2016/000011
§ 371 (c)(1),
(2) Date: Jul. 14, 2017

(87) PCT Pub. No.: WO2017/103954
PCT Pub. Date: Jun. 22, 2017

(65) Prior Publication Data
US 2018/0264705 A1    Sep. 20, 2018

(30) Foreign Application Priority Data

Jan. 16, 2015 (IT) .............................. VI2015A0011

(51) Int. Cl.
*B29C 49/04* (2006.01)
*A61M 5/31* (2006.01)
(Continued)

(52) U.S. Cl.
CPC ............. *B29C 49/04* (2013.01); *A61M 5/178* (2013.01); *A61M 5/3129* (2013.01);
(Continued)

(58) Field of Classification Search
None
See application file for complete search history.

(56) References Cited

U.S. PATENT DOCUMENTS 4,176,153 A * 11/1979 Weiler ...................... A61J 1/05
264/524
2009/0131864 A1 5/2009 Pickhard et al.
2012/0167528 A1 7/2012 Consolaro

FOREIGN PATENT DOCUMENTS

WO WO 2007/007178 A1 5/2009
WO WO 2014/090796 A1 6/2014

OTHER PUBLICATIONS

International Search Report and Written Opinion of the International Search Authority dated Jun. 17, 2016 in PCT/IT2016/000011.

* cited by examiner

*Primary Examiner* — Monica A Huson
(74) *Attorney, Agent, or Firm* — Hershkovitz & Associates, PLLC; Abe Hershkovitz

(57) ABSTRACT

The invention relates to a process for producing and assembling an aseptic container (100, 200) suitable for containing and supplying medical liquids comprising in sequence at least the steps of extruding a plastic material, operating on the intermediate tubular element obtained by blow moulding so as to obtain at least a hollow body (2, 202) and sealing the hollow body (2, 202) with a cap having a small size or applying an insert, comprising at least a portion (4, 204) with facilitated breakage.

24 Claims, 8 Drawing Sheets

(51) Int. Cl.
  *A61M 5/34* (2006.01)
  *A61M 5/178* (2006.01)
  B29C 49/20 (2006.01)
  B29L 31/00 (2006.01)
(52) U.S. Cl.
  CPC ............. *A61M 5/343* (2013.01); *B29C 49/20* (2013.01); *B29L 2031/7544* (2013.01)

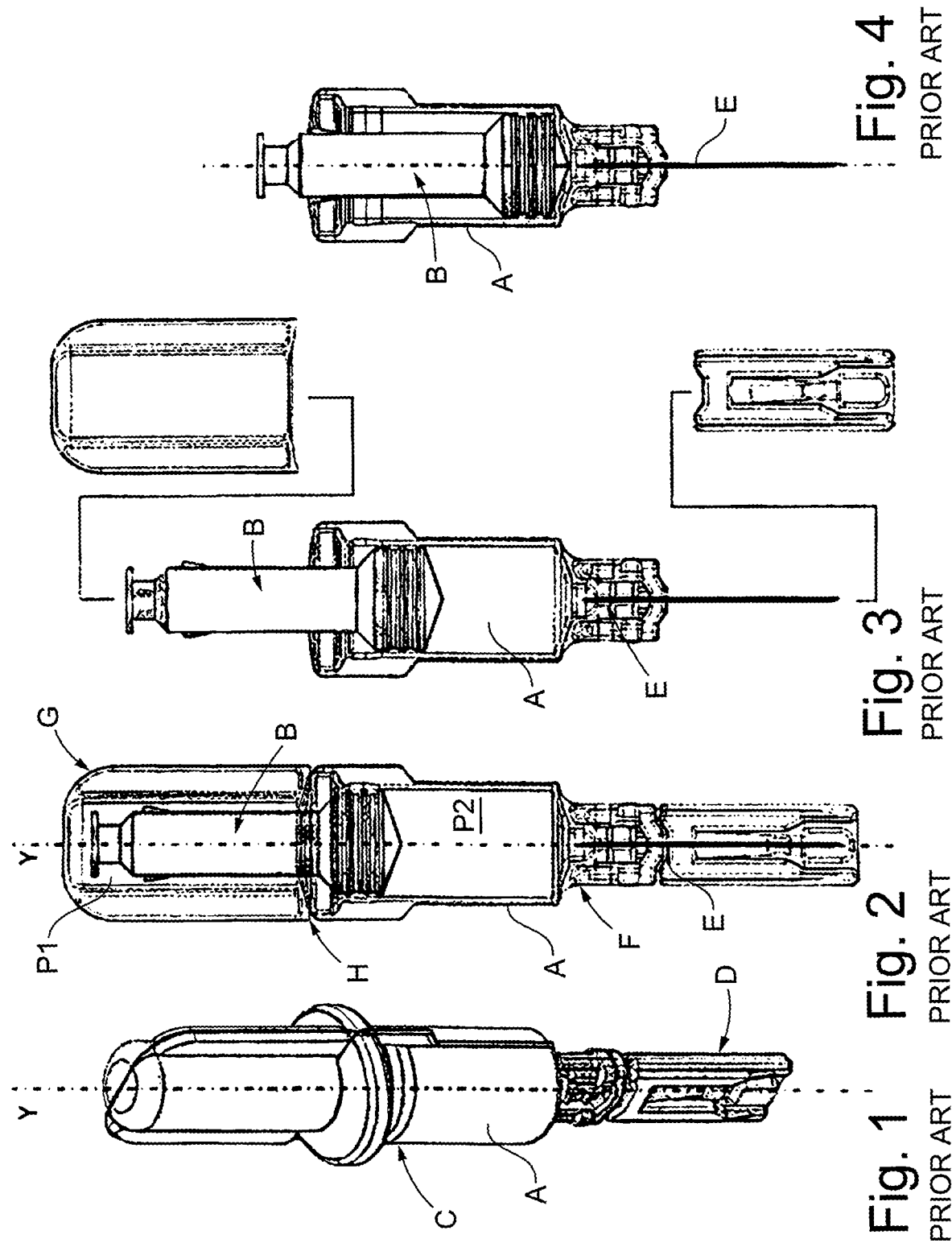

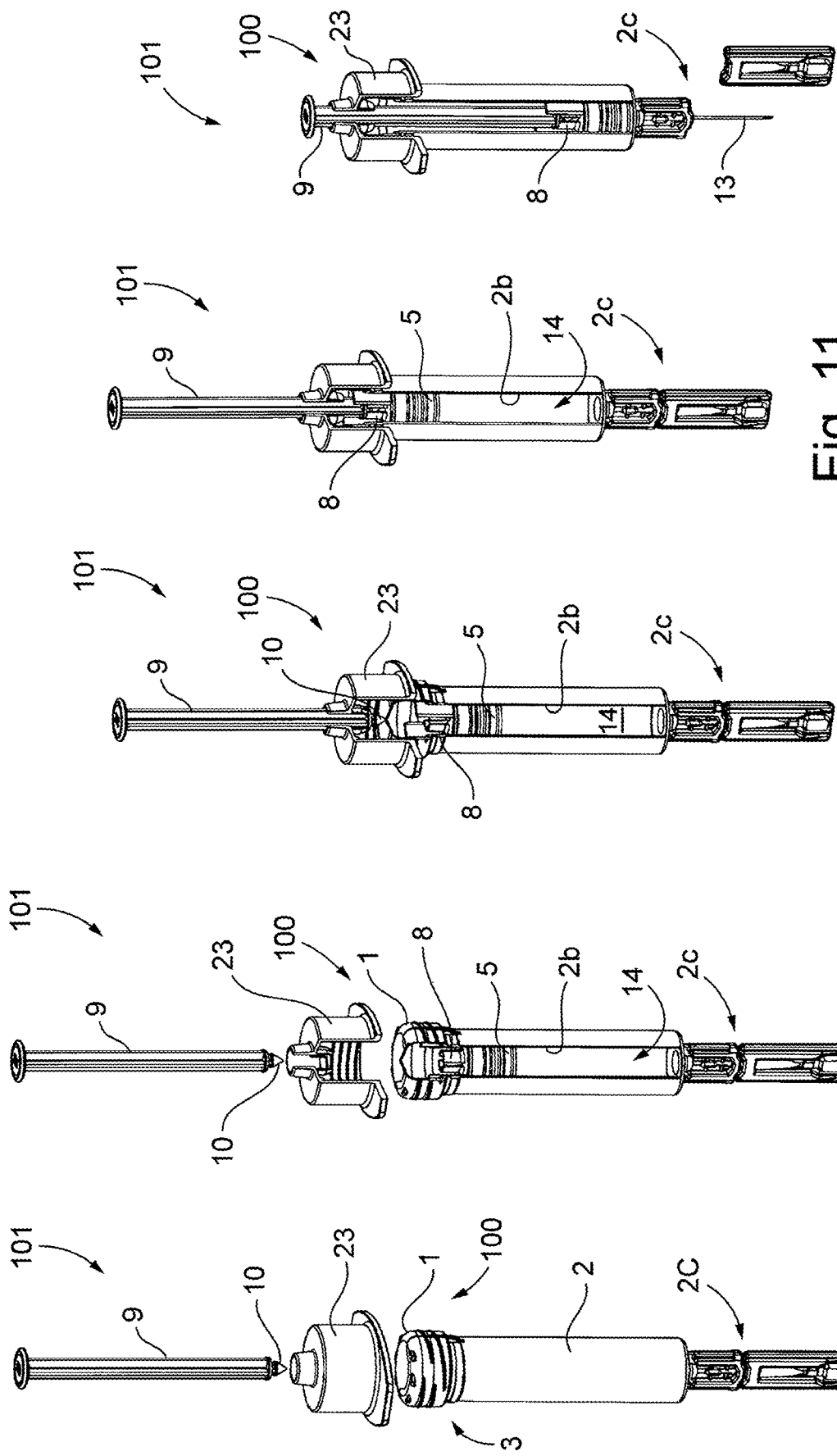

ASEPTIC CONTAINMENT DEVICE AND PROCESS FOR ITS PRODUCTION AND ASSEMBLY

The present invention relates to an aseptic containment device and, e.g. a syringe or a vial, and a process for its production and assembly; in particular, the invention relates to e.g. a vial or a syringe intended for containing a medical liquid to be injected, or an organic liquid which was extracted from organisms.

In detail, the invention refers to a syringe with a separate stem, which can be assembled at the moment of supplying the liquid.

A technology for producing syringes is known, from the patents n. WO2007007178 and WO2010143219. According to such technology, named BLOW FILL SEAL or BFS, the body of the container is at first formed embedding a first insert (a needle or a component for realizing the connecting part of the syringe), then filled with a desired liquid or solid, then a second insert is inserted (component of the syringe), and subsequently sealed.

The tight closure (or sealing: Seal step) occurs forming a cap or another closing element which is connected to the hollow body of the container and is movable by means of an area with reduced thickness, with facilitated breakage.

Such closing element has dimensions such to wholly cover the part of the stem that protrudes outside the body of the syringe.

E.g., common use pre-filled syringes are known, and shown in FIGS. 1-4, possibly provided with one or more inserts according to the abovementioned patents, comprising a hollow body A mainly set along a linear axis and filled with a liquid or medicine.

The syringes or medical devices which are concerned include moreover one pushing stem B, coupled to the hollow body A in correspondence of an access at a first end C of the latter.

At the second end there is a needle holder insert, alternatively a needle, applied to a restriction setting beak F.

A kind of tight closure for such known syringe comprises a cap G for protecting the stem B, so as it is kept sterile until the moment of the use, and having an area with reduced thickness in correspondence of a preset breaking point H, so that the opening occurs quickly and easily, always according to the abovementioned patents.

This technology allows advantageously making totally aseptic the obtained syringe for medical operations and enabling, therefore, a subsequent use under conditions of optimal security, hygienically and from the point of view of the human health for the involved people, patients and workers.

Still advantageously, the BFS production and assembly process allows obtaining a syringe for medical operations equipped with a high degree of sterilization faster than the prior art processes.

Moreover, the closing element has the advantage of being easily openable by a user, so that he can immediately access to the stem and then can use the syringe.

Nevertheless, such cap G covering the stem B has the drawback of proving expensive during production of the syringe, since it requires an additional consumption of plastic material.

Moreover, another drawback is due to the cost of price/volume of the stem B, which has to be treated aseptically in the steps of production, transport and storage.

Therefore, in case of large-scale productions, the consumption of plastic material for producing the syringe, the dimensions of the stem to be sterilized and subsequently stored and managed in the assembly lines, as well as their subsequent disposal, make the syringe ecologically, other than economically, unsustainable.

Still, such technology does not allow realizing grasping means enabling an easy handling by the fingers of a user. In particular, realizing pre-filled syringes with such technology, which are able to comply with ISO 7886 and 11040 with regard to the dimensions of the shaped handles for the fingers and of the free end of the stem, is very difficult.

In detail, the shaped handles must have appropriate dimensions, shape and strength for their intended purpose, i.e. allowing a safe hold of the syringe and a comfortable use.

Moreover, the stem of the syringe has to be such that, when the hollow body is hold in one hand, the stem may be pressed with the thumb of the same hand with a supporting surface big enough to make the operation comfortable for any worker.

In fact, according to the abovementioned technology BFS, all the elements are realized by only one mould and necessarily they are within a certain bulk, preventing shaped handles and the free end of the stem to escape from the volume of the hollow body so as to fit in the required standards.

The need for a syringe which allows the containing and the conservation of a substance, is easy to be opened by a user, meets the specifications required by the worker, but that at the same time proves ecologically and economically sustainable, still remains.

The present invention aims to avoid the drawbacks of the known art just complained.

In particular, the primary purpose of the invention is to develop a syringe and a process for its production and assembly that ensures the same syringe having a proper anatomical shape.

Moreover, one aim of the invention is realizing a syringe and a process for its production and assembly which allows obtaining a syringe complying with ISO 7886 and 11040 with regard to the dimensions of the shaped handles for the fingers and of the free end of the stem.

At the same time, aim of the invention is realizing an aseptic containment device for medical liquids and a process for its production and assembly which allows obtaining an aseptic containment device for medical liquids having aseptic conditions at least equal to the conditions of the ones obtained by the known BFS method.

Still, aim of the present invention is supplying an aseptic containment device for medical liquids and a process for its production and assembly which, compared to the known BFS technology, reduces the risks and the level of contamination of the components of the aseptic containment device for medical liquids and of the possible medical liquid which is contained within.

Another aim of the present invention is to devise an aseptic containment device for medical liquids and a process for its production and assembly which, while guaranteeing the achievement of the abovementioned aims, proves being quick to be implemented.

Further aim of the invention is supplying an aseptic containment device for medical liquids and a process for its production and assembly guaranteeing an use more workable for the worker or for the devices to which it is applied.

Said aims are reached by an aseptic containment device for medical liquids and a process for its production and assembly according to the attached independent claims 1, 15 and 23, to which referment is made, for the sake of brevity.

Further detail implementation characteristics of the process of the invention are highlighted in the respective dependent claims.

Advantageously, the process of the invention allows set up a container or a syringe for medical operations, also in its minimal configuration, with no manipulation of the components of the same syringe by the worker.

It allows e.g. making totally aseptic a syringe for medical operations and, therefore, subsequently using it under conditions of optimal security hygienically and from the point of view of health of the involved people, patients and workers.

Equally advantageously, this is reflected in a significant decrease in the production costs for a container or for a syringe for medical operations compared to the present technology, obviously for equal involved other factors.

Advantageously, moreover, the container and/or the syringe for medical operations which are obtained with the process for production and assembly of the invention have standard of performance at least equal to those of the containers and of the known syringes compared to which they have, however, the just highlighted advantages.

The aims and the said advantages, as well as others that will arise in the following, will appear more evidently from the following description regarding to a favourite embodiment of the process of the invention, given by way of example and as a guide, but not limiting to it, with reference to the attached drawings wherein:

FIG. 1 shows a syringe according to the known art in axonometric view;

FIG. 2 shows a cross section of the syringe of FIG. 1;

FIG. 3 shows a cross section of the syringe of FIG. 1 with cap and protecting element removed;

FIG. 4 shows a cross section of the syringe of FIG. 1 with piston at the end of the path;

FIG. 8 shows the syringe of FIG. 5 with the stem and the fingers support in a first step of assembly;

FIG. 9 shows one 3D cross section of the syringe of FIG. 5 with the stem and the fingers support in a first step of assembly;

FIG. 10 shows the syringe of FIG. 9 in a second step of assembly;

FIG. 11 shows the syringe of FIG. 9 in a third step of assembly;

FIG. 12 shows the syringe of FIG. 9 with protection device removed and piston at the end of the path;

Figure 7:
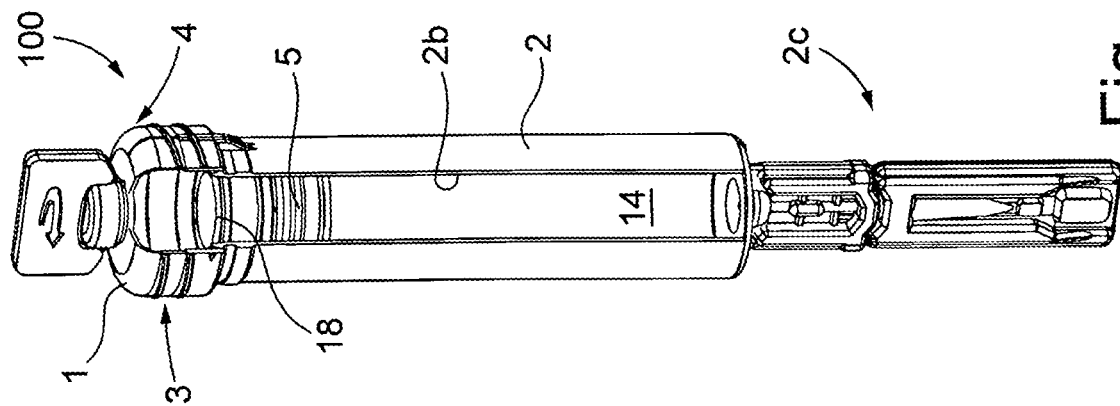
FIG. 7 shows one 3D cross section of a second embodiment of the syringe of the invention.

The aseptic containment device of the invention is schematically shown, in some of its possible variants, in FIGS. 5-24.

According to the invention, the process for its production comprises in sequence the following steps:

extruding plastic material at high temperature, e.g. 200° C., for obtaining an intermediate tubular element made of plastic material at least partially in the molten and/or malleable state, in common parlance known as "parison";

inserting the tubular element in one mould comprising two forming halves;

operating on the tubular element one moulding possibly preceded by blowing, so as to obtain at least a hollow body having one end having a main access closing the main access of the first end of the hollow body (step: SEAL) forming a tight closing device openable, comprising at least a facilitated breakage portion.

Preferably, if needed, it is possible, immediately before the step of closing the second hollow body, providing a step of stably inserting a sliding shaped seal within the hollow body in a time immediately following the step of filling.

In one variant of the invention, if needed, it is provided the filling of the hollow body (step: FILL), immediately after the step "BLOW" and immediately before the step of stably inserting a sliding shaped seal.

The just mentioned steps of extruding, blow moulding and inserting the sliding shaped seal occur continuously within the same industrial plant inside which ideal aseptic conditions are kept.

In a variant of the process of the invention, the step of closing the hollow body occurs by a so called Twist-Off (shown in FIGS. 7 and 13-16), for realizing an easy opening area, so as to allow the worker applying easily the open syringe to the different devices.

In another variant of the process of the invention, the step of closing the second hollow body occurs embedding also an insert having a membrane and/or a filter or filtering element, as shown in FIGS. 19-23.

In particular, the BFS technology for producing syringes consists in extruding a tubular element in plastic material at high temperature (the melting temperature of the same plastic material); in inserting it in one mould comprising two forming halves; a first part of the tubular element, which constitutes the lower part of the container, is closed in order to form a first hollow body of the container, embedding a first insert, e.g. a needle or another accessory, while a second part of the tubular element, which constitutes the head of the container, i.e. a second hollow body, is kept open for allowing to perform the following steps of the process.

Advantageously, such following steps last a few seconds, avoiding the cooling of the plastic material from its melting temperature.

The following standard steps of the BFS process comprise the blowing, the venting, the filling and the step of closing the second part or head (upper part) of the container.

According to the invention, preferably, before closing, the inserting of an small insert, engaged with a sliding shaped seal as an example a piston, in correspondence of the closing point, occurs.

The second hollow body of the syringe is closed with another mould in two forming halves.

Advantageously, the insert placed inside is used as support for the piston in order to prevent the latter from excessive movement, as an example the escape from the hollow body and for allowing the engagement with the separate stem.

In a favourite variant of the invention, a second insert 4A is provided, as shown in FIGS. 19-23, embedded in the closing device 1 of the syringe and placed within it. Such insert 4A is used as closing device equipped with membrane with facilitated breakage using a filter or a filtering element.

Figure 21:
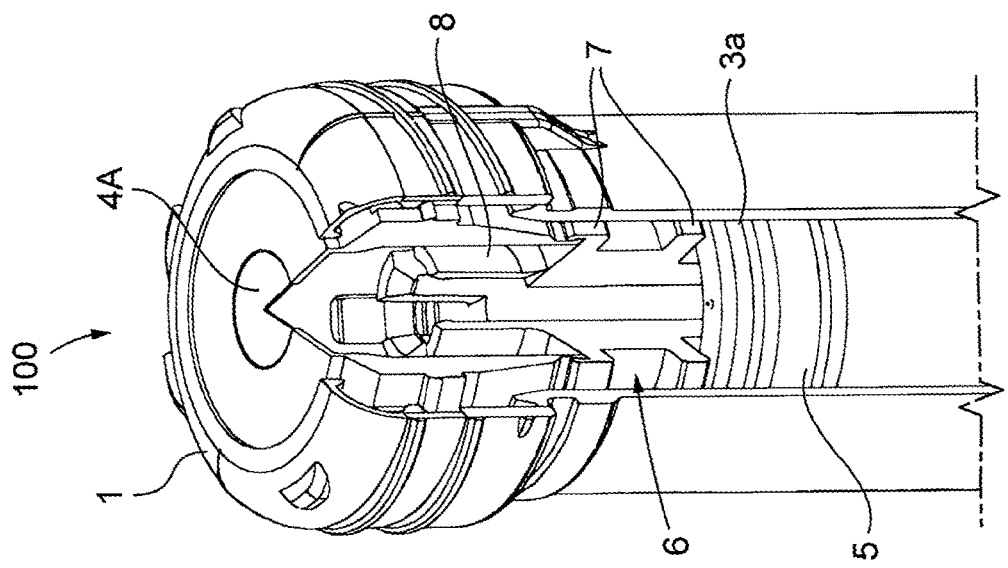
FIG. 21 shows one 3D cross section of a second variant of the invention.

In particular, in the FIG. 21 an insert 4A is shown, comprising a membrane with facilitated breakage constituted by a filter or filtering element able to make only air particles pass and to stop any other particle, comprising micro-organisms able to contaminate the inside of the syringe, before using it.

Figure 22:
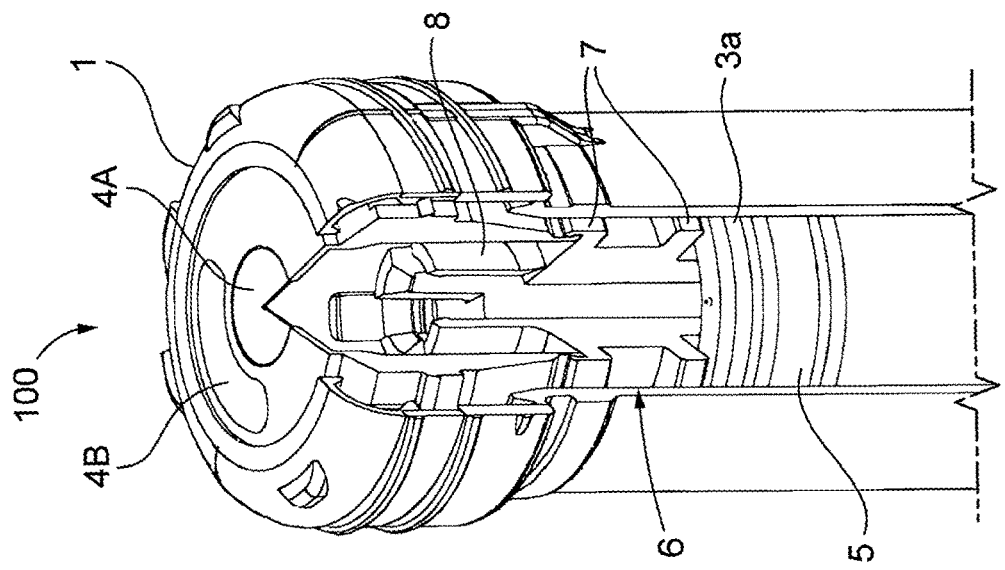
FIG. 22 shows one 3D cross section of a third variant of the invention.

In the FIG. 22 an insert 4A is shown, comprising a filter or filtering element 4B, placed at the side of a membrane with facilitated breakage.

Figure 23:
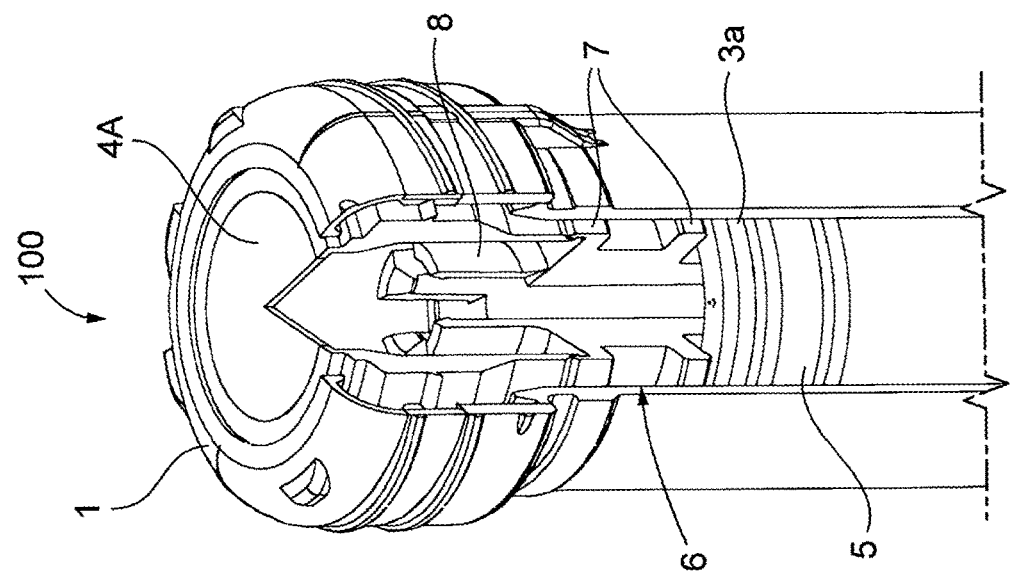
FIG. 23 shows one 3D cross section of a fourth variant of the invention.

In the FIG. 23 an insert 4A is shown, having at the centre a membrane with facilitated breakage.

The process, so modified, allows moreover significantly reducing the dimensions of the syringe during the production, with the obvious advantages relating to logistics and storage.

Finally, it is noted that the steps of blow moulding, calibrating the inner wall 2b of the hollow bodies, coupling the needle 13 with each one of the hollow bodies and filling the hollow bodies are performed by the shaped tools.

Moreover, as already said, each shaped tool is used for holding the needle 13 while it is inserted into the intermediate tubular element.

Besides calibrating the inner wall 2b of the hollow bodies, the shaped tools so allow obtaining another not insignificant advantage compared to the present technology.

In fact, during calibrating the inner wall 2b, the shaped tools cool down also the plastic material and, most importantly, the same inner wall 2b of the hollow bodies during forming step.

In such a way, the process of the invention realizes more quickly in respect with the known art the ideal conditions of absence or at least of minimization of risks of biological contamination for the medical liquid which is housed into the different hollow bodies.

Considering that the hollow bodies of the syringes are often filled with thermolabile chemical or biological products, so sensitive to the heat action as far as to losing their own characteristics, the advantage given by the present invention is evident.

For such products, thus, the invention reduces the waiting time for the inserting the liquid product into the medical container, with the obvious advantages implied by it in terms of efficiency.

Alternative variants of the process of the invention, non illustrate, may provide that only one or some of the steps of blow moulding, calibrating the inner wall of the hollow bodies, coupling a needle with each of the hollow bodies and filling the hollow bodies are performed by the shaped tool.

Figure 6:
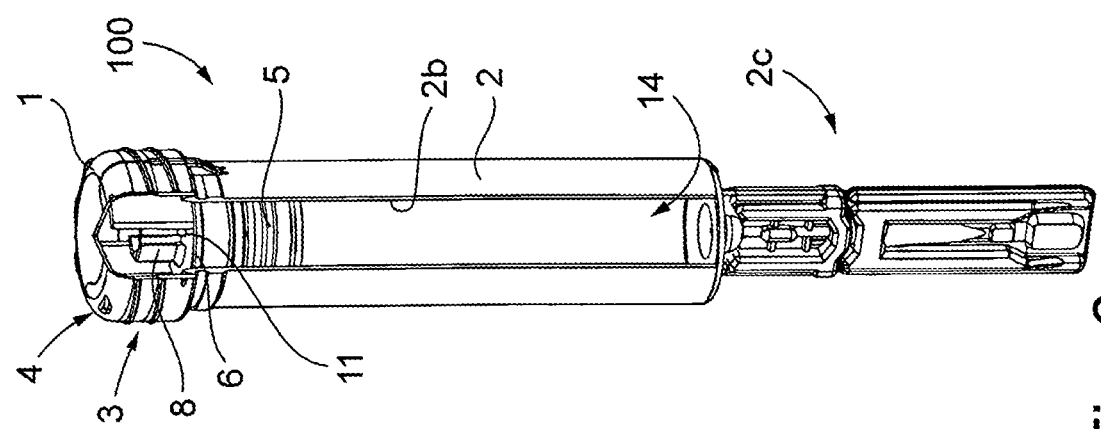
FIG. 6 shows one 3D cross section of the syringe of FIG. 5.
Figure 5:
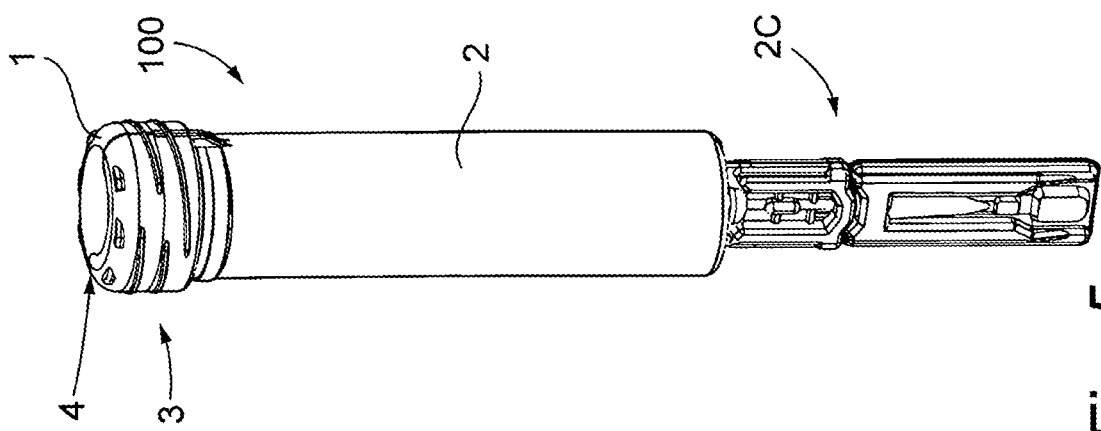
FIG. 5 shows a first embodiment of the syringe of the invention.
Figure 13:
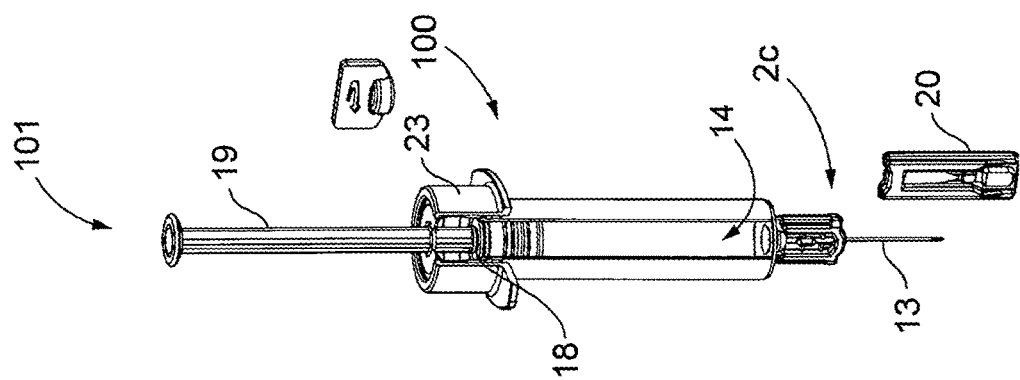
FIG. 13 shows one 3D cross section of the syringe of FIG. 7 with the stem and the fingers support in a first step of assembly.
Figure 14:
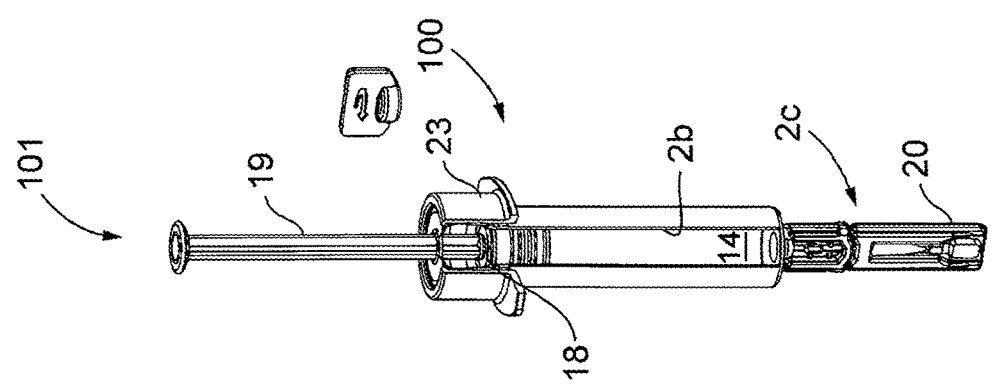
FIG. 14 shows the syringe of FIG. 13 in a second step of assembly.
Figure 15:
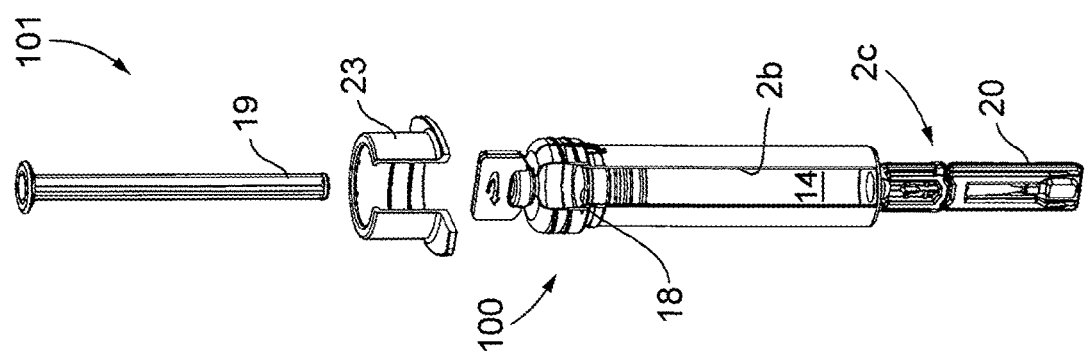
FIG. 15 shows the syringe of FIG. 13 in a third step of assembly.
Figure 16:
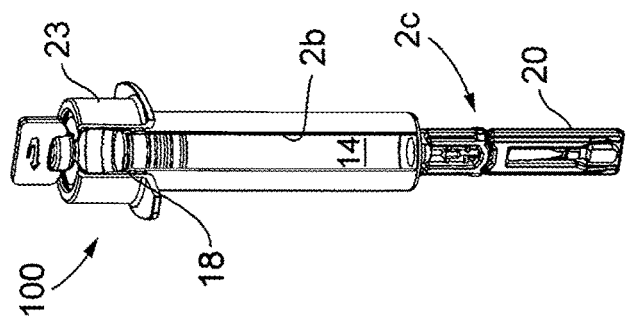
FIG. 16 shows the syringe of FIG. 13 in a fourth step of assembly, with protection device removed.

The base element for forming a syringe, obtained by the just described process and, since such, subject matter itself of the present invention, shown in figures with the numerical reference 100, is shown in a first of its embodiments in FIGS. 5 and 6.

The base element 100 of the figures comprises a closing element 1 for closing/protecting the second hollow body 2, which can be empty or filled with a liquid or medicine.

In detail, in FIGS. 5 and 6 a closed base element 100 is shown, with the closing element 1, e.g. having a thin section, formed on the second hollow body 2 in correspondence of its first end 3, having an area 4 possibly with no central seams, realizable possibly according to the known system shown in the document PCT/IB2006/001963 so as to have a section with reduced thickness, weakening the mechanical strength of the body of the closing element 1, so as the user is able to punch it without difficulty.

The closing element 1 has internally a sliding shaped seal or piston 5, e.g. one syringe plunger, joined with an insert 6 equipped with one or more flaps 7 so as to prevent the piston 5 from totally escaping from the second hollow body 2.

Such insert 6 has moreover retaining elastic means 8 suitable for engaging, irreversibly, unless ruining its functionality, with one stem 9 (shown in FIGS. 8-12, 17-20), e.g. one pushing stem, having in turn a shaping 10, e.g. as shown in figures in a narrow shaped configuration.

In particular, the closing element 1 is initially used as protection of the insert 6, so as the latter cannot be unintentionally tampered during the transport, nor when it is not the right moment.

Moreover, for realizing a syringe 101, grasping means 23 can be provided, advantageously suitable for being coupled with the hollow body 2 subsequently to the step of sealing the access 11, and then realizable with one separate mould.

This allows to not restrict the dimensions of the grasping means 23 and, in particular, allows realizing such grasping means 23 complying with ISO 7886 and 11040 with regard to the dimensions of the shaped handles for the fingers and of the free end of the stem.

In the same way, it is possible assembling possibly the pushing stem 9 in a second moment with the base element 100, the pushing stem 9 being separately realizable and then advantageously complying with ISO 7886 and 11040 with regard to the dimensions of the shaped handles for the fingers and of the free end of the stem.

In a favourite variant of the base element 100 of the invention, shown in FIGS. 7, 13-16, the closing element 1 has a twist off element for facilitating the opening of the syringe by a worker.

According to the invention, the sliding shaped seal 5 is inserted in the corresponding hollow body 2 through the main access 11 at the first end 3 of the hollow body 2, placing the plunger of the sliding shaped seal 5 inside this.

Preferably but not necessarily, the process of the invention comprises the step of calibrating the inner wall 2b of the hollow bodies, performed before the step of inserting the sliding shaped seal 5 in the respective second hollow body 2 and, in practice, simultaneously with the step of extruding, while the different hollow bodies are still heated and at least partially in molten and/or malleable state.

In each case, at the same time but not necessarily subsequently to the step of inserting the sliding shaped seal 5, it is possible also to insert retaining means as the insert 6 and/or an insert with membrane and/or filter 4A, respectively suitable for avoiding the escape of the sliding shaped seal 5 or at least of the plunger from the hollow body 2 and for realizing an passage area for the air and a membrane with facilitated breakage.

More in detail, the insert 6 comprises retaining means 8, e.g. a substantially annular element (as shown in detail in FIGS. 20-23) placed in correspondence of the access 11, and/or one or more shaped fins 7 protruding from the external wall 3a of the sliding shaped seal 5.

Alternatively to the annular element 8, providing a match 18 (shown in FIGS. 7 and 13-16) on the inner surface of the hollow body 2 in correspondence of its upper end 3 is possible.

In a favourite variant of the base element 100 of the invention, shown in FIGS. 19-20-21-22-23, the closing element 1 has an insert 4A with facilitated breakage, in particular having a membrane and/or embedded filter for facilitating the opening of the syringe by a worker, as previously described.

According to the invention, an insert 4A with membrane and/or filter is inserted into the corresponding hollow body 2 through the main access 11 at the first end 3 of the hollow body 2, and embedded in the closing device 1.

The step of extruding and the step of blow moulding occur within a forming mould of the type per se known in this sector.

The forming mould has in this case a plurality of cavities, not shown for convenience, each of which having the external profile reproducing the predetermined shape of the respective hollow body 2.

More in detail, the forming mould includes first of all two half shells facing and opposing each other.

The forming mould is opened both during the step of extruding, keeping the half shells apart from the intermediate tubular element, both during the step of inserting the shaped tool in the intermediate element, drawing between them the half shells and placing them close to the intermediate element.

Therefore, the step of pressing the intermediate tubular element on the shaped tools consists in the step of closing the lower part of the forming mould placing the half shells near each other interposing the intermediate tubular element and the shaped tools for at least a longitudinal portion of the same half shells.

In a preferred but not binding manner, the process of the invention comprises the step of coupling, with the second end 2c, opposed to the first end 3, of each one of the hollow bodies, a needle for injections 13 communicating with the internal volume 14 of the respective hollow body 2, performed simultaneously with the step of blow moulding and with the step of calibrating the inner wall 2b of the hollow bodies.

More precisely, the needle 13 is coupled to a restriction setting beak, made in the second end 2c of each of the hollow bodies by the forming mould.

In this respect, the process of the invention comprises the preparatory operation of inserting, by means of the shaped tools, the needle 13 within the intermediate tubular element, performed before the actual operation of coupling the needle 13 with the second end 2c of the corresponding hollow body 2 and simultaneously with the step of inserting the shaped tools into the intermediate tubular element.

According to the herewith described favourite embodiment of the invention, the process may comprise the step of filling the hollow bodies with a medical liquid so as to obtain empty or single-dose prefilled syringes for injections.

If desired, the step of filling the hollow bodies with the medical liquid is performed after the step of blow moulding the hollow bodies and before the step of inserting the sliding shaped seal 5 within a respective hollow body 2.

Advantageously, the process of the invention includes the step of sealing the main access 11 at the first end 3 of the hollow body 2, performed after the step of stably inserting the sliding shaped seal 5 into the same hollow body 2.

The tight closure (or sealing: obtained during the step Seal) occurs forming a cap with small dimensions, immovable, contrary to what was realized up to now according to the known technology, but with facilitated breakage; such cap, or closing element, has an easily punchable area, in particular with reduced thickness.

According to the invention, the closing device 1 comprises at least an area 4 (shown in detail in FIGS. 5-6) of its surface realized with reduced thickness, or, in a favourite variant of the invention (shown in FIGS. 19-23), the tight closure (or sealing: obtained during the step Seal) occurs forming a cap having a small size embedding an insert 4A. According to the invention, such insert is equipped with an absolute sterilizing filter comprising pores of maximum dimension of 0.45 µm or alternatively such filter may have different degrees of porosity according to the needs.

Advantageously, this last operation sets, substantially, to package a base element 100 for realizing a syringe for medical operations 101, in a seamless manner compared to the other above described operations, involving the production the filling and assembling the base element 100, keeping aseptic the filling liquid.

In fact, the execution of such step of sealing the portion of the sliding shaped seal 5 directly at the plant of the manufacturer of the base element 100 actually removes the step of final wrapping now implemented on the known syringes at the manufacturer's of medical liquid.

As a consequence, this aspect of the invention helps reducing, compared to the present art, the tampering of the components of the base element by the workers, extremely reducing the risks of contamination both of the same components and of the medical liquid introduced into the hollow body of the base element 100 alike, besides making operationally easier and quick the complete production of the syringe 101.

The step of sealing the main access 11 occurs by the known system, but using a cap or closing device 1 with small dimensions, in particular e.g. comparable to a disc, possibly, as shown in FIGS. 19-23, with embedding an insert 4A and/or with a membrane with facilitated breakage.

In addition, it is clarified that the whole just described process, consisting of the steps of extruding the intermediate element, blow moulding for obtaining the hollow bodies, calibrating the inner wall 2b of each of the latter, coupling a needle 13 to each of the hollow bodies, filling the hollow bodies, inserting a sliding shaped seal 5 into the hollow body 2 and sealing the main access 11, occurs in a period together totalling a maximum of 50 seconds.

Moreover, the process of the invention may comprise also a step of assembling grasping means 23 to the hollow body 2, subsequently to the step of sealing the access 11; in fact the grasping means 23 according to this just described process are advantageously realizable also with one separate mould.

This allows to not restrict the dimensions of the grasping means 23 and, in particular, allows realizing such grasping means 23 complying with ISO 7886 and 11040 with regard to the dimensions of the shaped handles for the fingers and of the free end of the stem.

In the same way, it is possible to assemble in a second moment to the base element 100 also one pushing stem 9 or 19, separately realizable and then advantageously complying with ISO 7886 and 11040 with regard to the dimensions of the shaped handles for the fingers and of the free end of the stem.

In particular, e.g. as shown in FIGS. 8-12 and 19-20, it is possible realizing separately one pushing stem 9 having the dimensions complying with the abovementioned ISO and having a shaping 10 corresponding to the shaping of the sliding shaped seal 5 or—preferably—to the shaping of the retaining elastic means 8 of a shaped supporting element integral with the sliding shaped seal 5, e.g. the insert 6 shown in figures.

Similarly, also the grasping means 23 may be realized separately, and in particular (as shown in detail in FIGS. 19 and 20) comprising a shaped annular element 24, which can be placed around the hollow body 2 and having two lateral fins 25 for gripping by the fingers of the user; the pushing stem 9 may be supplied already coupled to it, sliding through a central hole 26 of the shaped annular element 24 for making the application to the upper part of the hollow body 2, in correspondence of the closing disc 1, easier; in particular, the shaped annular element may have a match for preventing the same shaped annular element 24 from sliding along the hollow body 2, and protruding elements, corresponding to matches on the hollow body 2, so as to stop the movements of the shaped annular element 23 along the hollow body once its working position is reached.

Alternatively, it is possible providing in correspondence of the first end 3 of the hollow body 2 a thread 15, corresponding to a counter thread 16 on the grasping means 23, so as to facilitate their fixing on the hollow body 2 in the right working position.

In such a way, in detail, at the end of the path the shaping 10 of the stem 9 gets stuck in the counter shaping of the retaining elastic means 8 of the sliding shaped seal 5 after the part 4 of the surface of the closing device 1 is broken; or, at the end of the path, the shaping 10 of the stem 9 is close to the part 4 of the surface of the closing device 1, so that, exerting an adequate pressure, the user of the syringe 100 is able to break such part 4 with only one hand and then to supply the liquid which is contained in the base element 100.

In such case, the shaped annular element 23 may comprise a cylindrical portion 27 having dimensions corresponding to those of the pushing stem 9, so as such cylindrical portion 27 acts as guide for the same, in order to direct the shaping 10 of the pushing stem 9 towards the exact breaking point, coincident with the position of the reduced thickness area or of the filtering membrane 4, of the closing device 1.

In this way, the user willing to use a prefilled syringe obtained by the process of the invention, shall handle with one hand the hollow body 2 sealed by the closing device 1 and with the other hand the pushing stem 9 supplied separately (or in the same kit); exerting a pressure on the reduced thickness area 4 of the closing device 1, the shaping 10 of the pushing stem 9 breaks the same closing device 1, and contacts the shaping of the retaining elastic means 8 of the shaped supporting element 6, shaped so as to house the shaping 10 and possibly to stop the escape with possible matches; at that point the pushing stem 9 gets integral with the sliding shaped seal 5 and with only one hand the user may supply the liquid like when handling a traditional syringe.

Of course, it is possible that the shaping of the retaining elastic means 8 equipped with matches is directly on the sliding shaped seal 5, making the shaped supporting element 6 superfluous.

Nevertheless, advantageously, the shaped supporting element 6 may be realized in a material more rigid than the one to be used for the sliding shaped seal 5, for obvious functional reasons.

As already mentioned above, in the variant of the invention shown in FIGS. 7 and 13-16, the opening occurs by exerting a torque force on the closure of the twist-off type, making the shaping 10 of the stem 9 narrow shaped (as shown in the other figures) no more required, but one pushing stem 19 without such shaping is enough, possibly only suitable for engaging in a match 18 on the inner surface of the hollow body 2.

In each case, the pushing stem 9 or 19 is able to push the sliding shaped seal 5 towards the second end 2c of the hollow body 2 so as to supply the medical liquid contained within.

Figure 17:
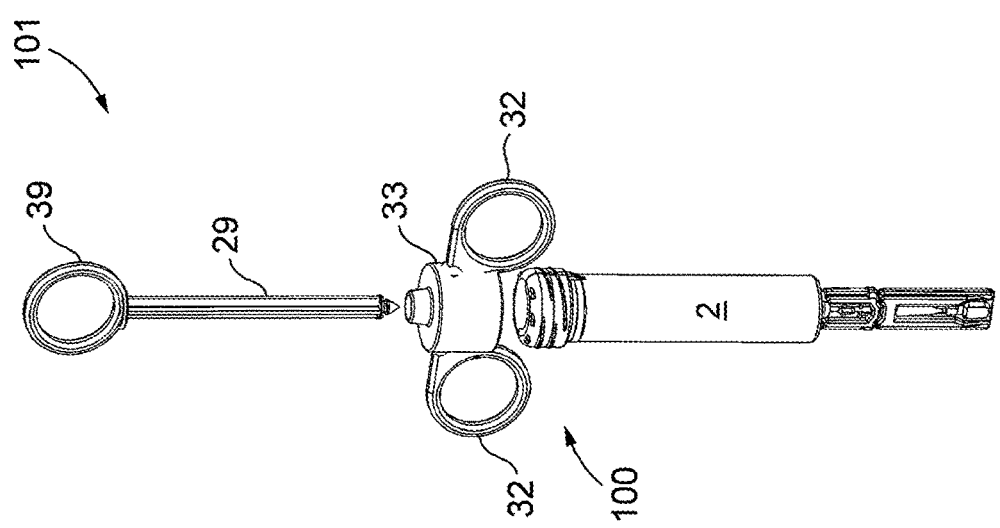
FIG. 17 shows the syringe of FIG. 5 with the stem and a variant of the fingers support in a first step of assembly.
Figure 18:
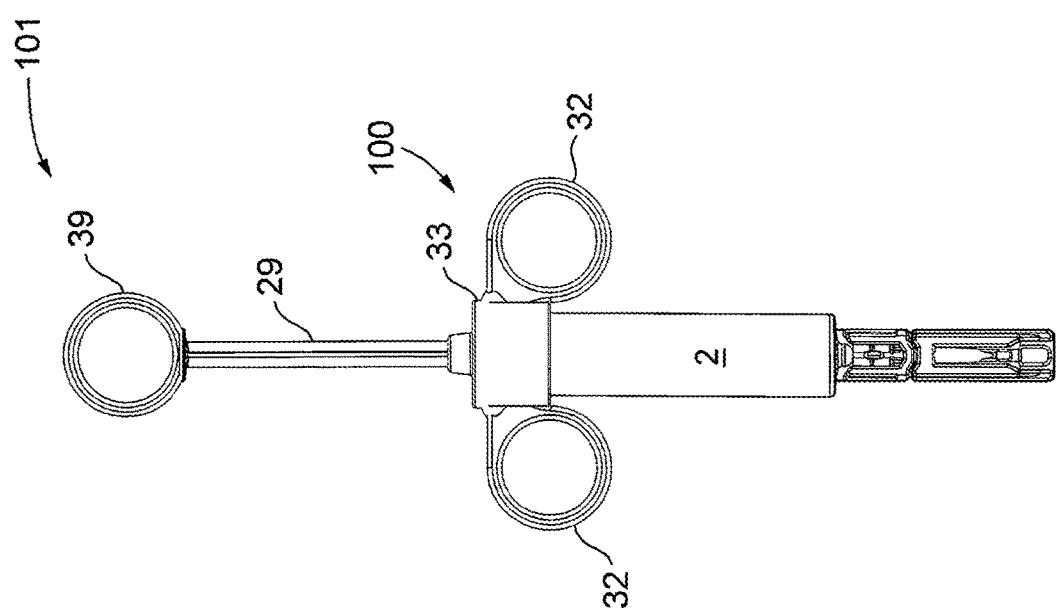
FIG. 18 shows the syringe of FIG. 17 in a second step of assembly.

In another variant of the invention, shown in FIGS. 17 and 18, a support for the fingers 33 and one stem 29 may be applied to the base element 100, the support for the fingers 33 and the stem 29 being realizable separately and thus having the desired dimensions, equipped with rings 32 and 39 so as to allow a safe handling for the doctor for performing the injections, and to push the sliding shaped seal 5 towards the second end 2c of the hollow body 2 so as to supply the medical liquid contained within.

Figure 18A:
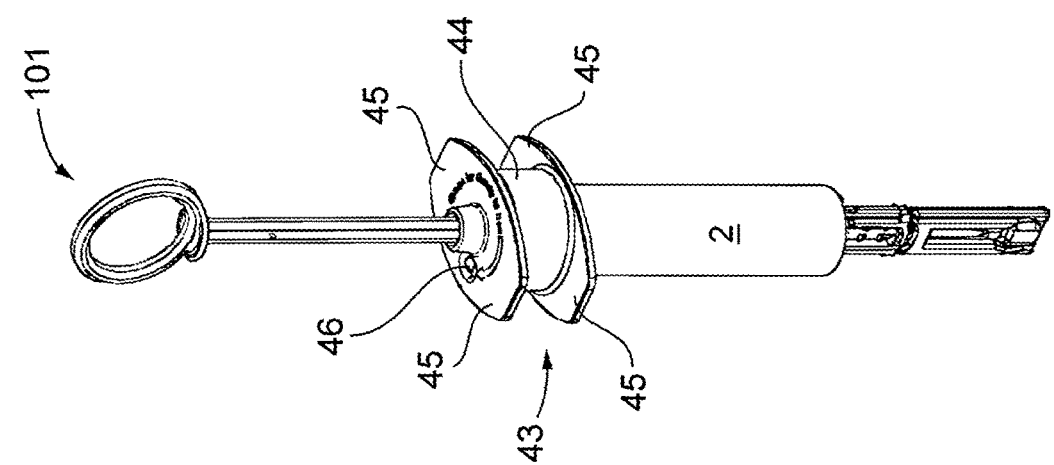
FIG. 18A shows the syringe of FIG. 18 in one of its variants.
Figure 20:
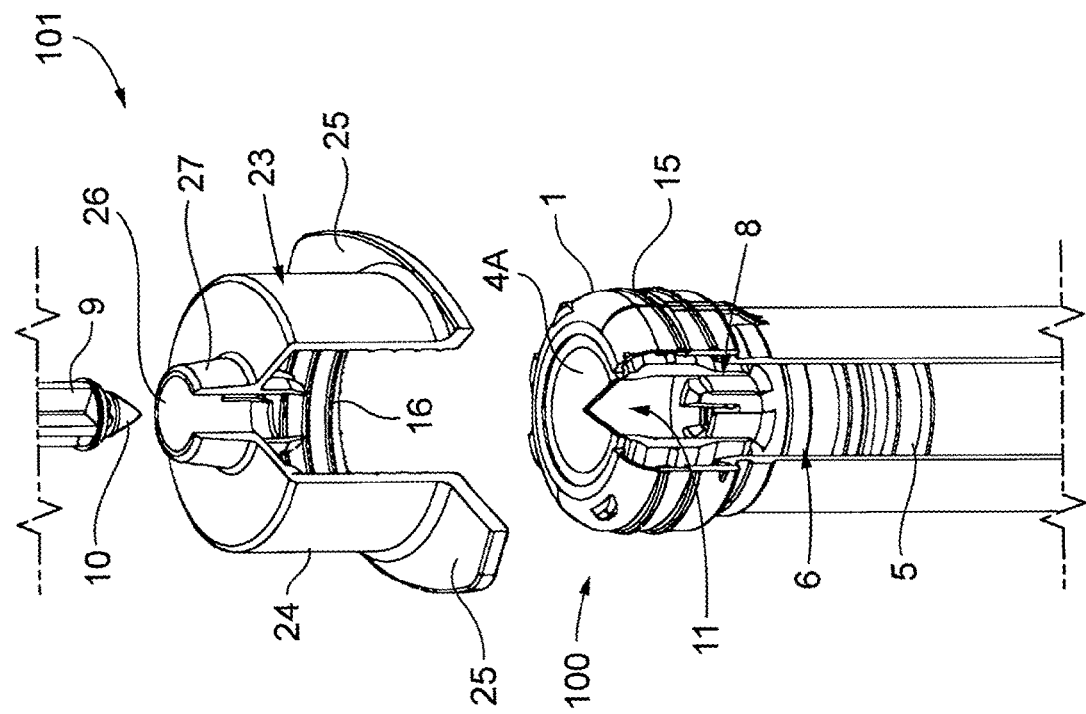
FIG. 20 shows one 3D cross section of the FIG. 19.
Figure 19:
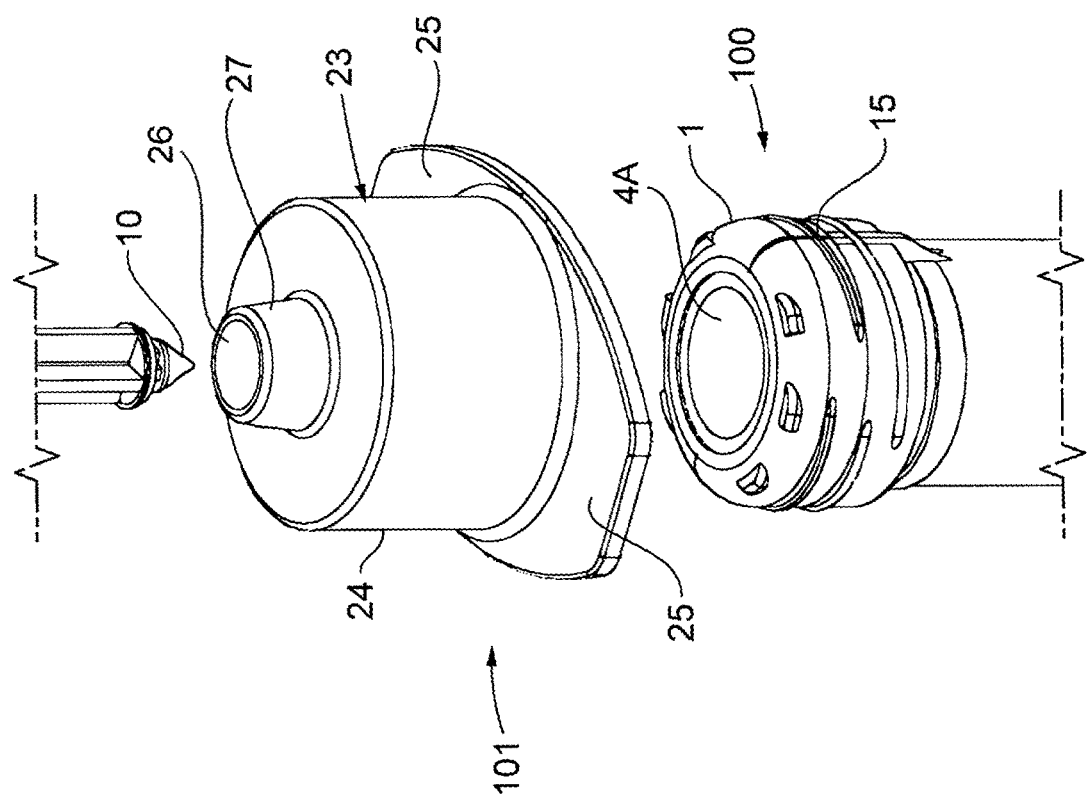
FIG. 19 shows an enlarged detail of a first variant of the invention.

In another variant of the invention, shown in the FIG. 18A, it is possible applying to the base element 100 grasping means 43, similar to those which were described up to now, and comprising in particular a shaped annular element 44, which can be placed around the hollow body 2, having four lateral fins 45, two by two parallel to each other, for gripping by the fingers of the user, so as each of the fingers may be placed between each couple of fins 45 parallel to each other; advantageously, the couples of lateral fins 45 parallel to each other allow the user pushing the sliding shaped seal 5 (not shown in FIG. 18A) in both directions, or only towards the second end 2c of the hollow body 2, so as to supply the medical liquid contained within or—if needed—to withdraw a medical liquid, always with the use of only one hand.

Moreover, in a further variant, shown e.g. in FIG. 18A in combination with the previous variant, there may be also a pointer 46, suitable for pointing out the proper location of the grasping means 43 in respect with the base element 100 during their assembly, so as to guarantee a right use of the syringe 101.

The base element 100 comprises, moreover, the needle 13, coupled to the restriction setting beak of the hollow body 2 by joining means, made up of the plastic material which, still at the molten state, is pressed between the main half shells of the forming mould during the process for blow moulding.

The needle 13 is, also, completely covered with protection means, numbered as a whole with 20, externally applied to the needle 13 and made monolithic with the hollow body 2 during the above said process for blow moulding, which realize in practice a sort of a cap for the needle 13, in not use conditions of the syringe 101. More in particular, the protection means 20 comprise a laminar capsule made of plastic material which, in correspondence of the hollow body 2, comprises weakening lines, not visible, for allowing its practical, easy and quick release from the hollow body 2 when the syringe 101 has to be used.

In a favourite variant of the base element 100 of the invention, shown in FIGS. 19-20-21-22-23, the base element 100 has a closing device 1 having an insert 4A, with membrane and/or filter, embedded in the same closing device. Such insert 4A is realized for facilitating the opening of the base element 100 by a worker and, if equipped with filter, allows having a passing area for sterile air and a membrane with facilitated breakage.

Substantially, thus, the base element 100 obtained with the process of the invention comes out already packaged, according to the configuration shown in FIGS. 5-7 13, and does not require further steps, works or treatments for being placed on the market.

From the description just made, it is understood, therefore, that the basic element, the syringe and the process for its production and assembly, subject of the present invention, achieve the aims and realize the advantages already mentioned.

During execution, changes to the process of the invention can be made consisting, for example, in obtaining a single hollow body by the step of blow moulding, e.g. using a mould forming a single cavity.

In such case, the operating modes described above of the process of the invention will vary in accordance.

It should also be noted that the present invention, while being described with particular reference to a single use pre-filled syringe for injections, also extends to liquid containers.

In this case, simply delete the step of inserting one or more inserts and go directly to the step of inserting the liquid and embedding only the insert 4A with the filtering element, providing one suitable mould.

It's clear that numerous other variants may be made to the process in question, without for this departing from the novelty principles inherent in the inventive idea expressed here, as it is clear that in the practical implementation of the invention, the materials, the forms and the dimensions of the details illustrated may be any, according to the needs, and replaced with others technically equivalent.

Figure 24:
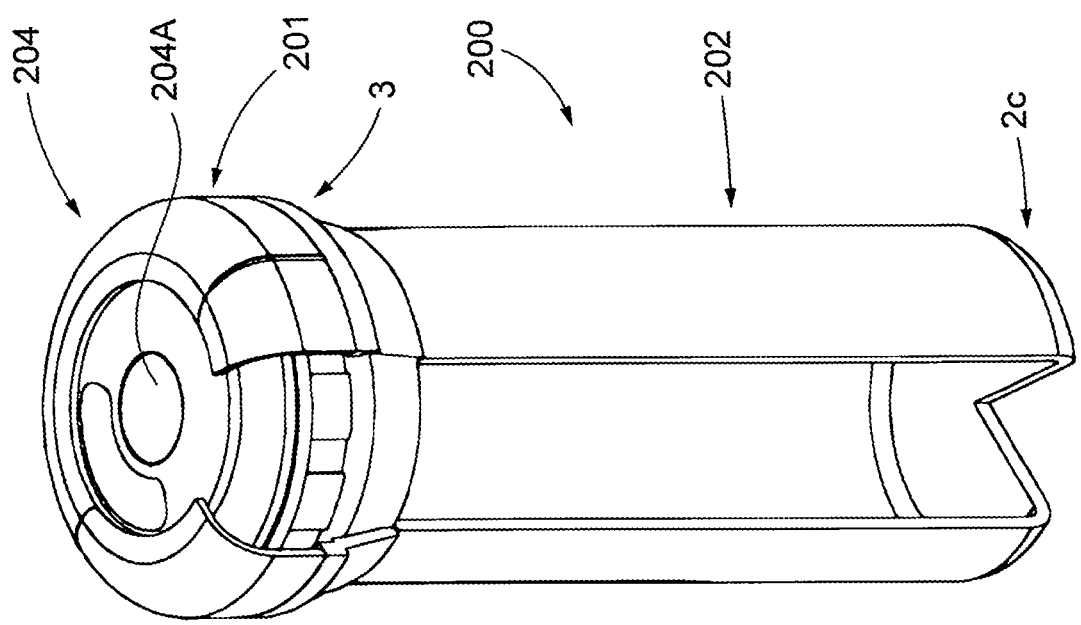
FIG. 24 shows one 3D cross section of an alternative embodiment of the invention.

E.g., as shown in FIG. 24, it is possible to realize a tight container 200 for medical liquids, e.g. a vial, realizable according to the process above described, during which the steps of inserting at least one of the inserts or the sliding shaped seal are not performed, and providing a step of embedding in the tight container 200 an insert 204 with facilitated breakage. In particular, the insert 204 with facilitated breakage may be realized also with a filtering element 204A, as those already described for the previous embodiments of the invention.

In particular, in the FIG. 24 a closed vial 200 is shown, with the closing element 201, e.g. having a thin section, formed on the hollow body 202 in correspondence of its first end 3, having an area 204 also with no central seams, weakening the mechanical strength of the body of the closing element 201, so as the user is able to punch it without difficulty.

Where the constructive characteristics and the techniques mentioned in the subsequent claims are followed by reference signs or numbers, such reference signs have been introduced with the only aim of increasing the intelligibility of the claims and, therefore, they do not have any limiting effect on the interpretation of each element identified, purely by way of example, by such reference signs.

The invention claimed is:

1. Process for producing and assembling an aseptic container suitable for at least one of, containing and supplying medical liquids, the container including a hollow body and a main access suitable for being traversed by an operating stem, the process comprising in sequence:
   extruding plastic material for obtaining an intermediate tubular element made of plastic material at least partially in at least one of, a molten and malleable state, said intermediate tubular element having a first end and a second end;
   operating on said intermediate tubular element a blow moulding so as to obtain at least a hollow body, the first end having a main access;
   sealing said main access of said first end of said hollow body forming an openable and immovable tight closing device, said tight closing device comprising at least a facilitated breakage portion; and
   embedding a facilitated breakage insert in the tight closing device, and in that the facilitated breakage insert is made of a sterilizing filter.

2. Process according to claim 1, wherein said extruding and said moulding occur within a forming mould having one or more cavities, each having the external profile reproducing the predetermined shape of said hollow body, said mould comprising at least two main half shells facing and opposing each other.

3. Process for producing and assembling an aseptic container suitable for at least one of, containing and supplying medical liquids, the container including a hollow body and a main access suitable for being traversed by an operating stem, the process comprising in sequence:
   extruding plastic material for obtaining an intermediate tubular element made of plastic material at least partially in at least one of, a molten and malleable state, said intermediate tubular element having a first end and a second end;
   operating on said intermediate tubular element a blow moulding so as to obtain at least a hollow body, the first end having a main access;
   sealing said main access of said first end of said hollow body forming an openable and immovable tight closing device, said tight closing device comprising at least a facilitated breakage portion;
   forming an openable and immovable tight closing device, immediately after operating on said intermediate tubular element a blow moulding so as to obtain at least a hollow body, and immediately before sealing said first end of said hollow body,
   stably inserting a sliding shaped seal within said hollow body through the first end of said hollow body at a time immediately following said blow moulding.

4. Process according to claim 3, further comprising calibrating at least a longitudinal portion of the inner wall of said hollow body, performed before said inserting said sliding shaped seal into said hollow body and after said extruding, while said hollow body is still hot and in said at least partially at least one of, molten and malleable state.

5. Process according to claim 4, wherein said calibrating said inner wall of said hollow body comprises pressing said intermediate tubular element onto at least a shaped tool which was previously inserted within said intermediate tubular element obtained by said extruding plastic material.

6. Process according to claim 5, wherein said forming mould is opened both during said extruding, keeping said main half shells apart from said intermediate tubular element, while inserting said shaped tool in said intermediate tubular element, drawing said main half shells near each other and placing said main half shells close to said intermediate tubular element.

7. Process according to claim 5, wherein the pressing of said intermediate tubular element onto said shaped tool comprises closing said forming mould, placing said main half shells near each other interposing said intermediate tubular element and said shaped tool for at least a longitudinal portion of said main half shells.

8. Process according to claim 4, further comprising coupling, with the second end of said hollow body, opposed to said first end, one of, a needle or insert for other types of connections for at least one of, injections and samples communicating with the internal volume of said hollow body, performed simultaneously with said blow moulding and with said calibrating said inner wall of said hollow body.

9. Process according to claim 8, further comprising inserting said needle within said intermediate tubular element by said shaped tool, performed before coupling said needle with said second end of said hollow body and simultaneously with said inserting said shaped tool in said intermediate tubular element.

10. Process according to claim 3, further comprising filling said hollow body with a medical liquid after blow moulding said hollow body and before inserting said sliding shaped seal within said hollow body.

11. Process according to claim 3, including, between inserting the sliding shaped seal and sealing the first end, forming a retainer for avoiding the escape of the sliding shaped seal from the hollow body.

12. Process according to claim 11, wherein said retainer comprises:
an annular element placed in correspondence of at least one of the main access and one or more shaped fins protruding from the sliding shaped seal.

13. Process according to claim 8, wherein at least one of said blow moulding, calibrating said inner wall of said hollow body, coupling said needle with said hollow body and filling said hollow body is performed by said shaped tool.

14. Base element for a tight container for containing medical liquids, the element comprising a hollow body equipped with a main access suitable for being punched, comprising an immovable and openable tight closing device in correspondence of said main access, by the process according to claim 3, and wherein the closing device comprises at least a facilitated breakage portion.

15. Base element for an aseptic container equipped with an operating stem and suitable for at least one of, containing and supplying medical liquids by said operating stem, the element comprising a hollow body equipped with a main access suitable for being traversed by said operating stem, and a sliding shaped seal within said hollow body, said element comprising an immovable and openable tight closing device in correspondence of said main access, for allowing the inserting of said operating stem, in that said sliding shaped seal is equipped with coupling moans a coupler for coupling with the operating stem, and in that the closing device comprises at least a facilitated breakage portion.

16. Element according to claim 14, wherein said tight closing device is pierceable.

17. Element according to claim 16, wherein said closing device comprises an area with reduced thickness.

18. Element according to claim 16, wherein said closing device comprises a facilitated breakage insert, and in that the facilitated breakage insert is made up of a sterilizing filter.

19. Element according to claim 18, wherein said sterilizing filter is an absolute filter, and in that it comprises pores of maximum dimension of 0.45 μm.

20. Element according to claim 18, wherein the filter comprises pores of a dimension greater than 0.45 μm.

21. Element according to claim 15, wherein said tight closing device has an immovable portion.

22. Element according to claim 21, wherein said tight closing device comprises a closing device of the twist-off type.

23. Kit for forming a medical syringe, comprising an element according to claim 15, and at least one of the following: a grasping device suitable for being coupled with the hollow body of the element, and a pushing stem suitable for pushing a sliding shaped seal along the hollow body.

24. Kit for forming a medical syringe, according to claim 23, comprising a grasping device suitable for being coupled with the hollow body of the element, equipped with a pointer suitable for pointing out a proper location of the grasping device with respect to the element.

* * * * *